United States Patent [19]

Sorensen

[11] Patent Number: 4,877,798

[45] Date of Patent: Oct. 31, 1989

[54] TREATMENT OF FIBROMYALGIA

[75] Inventor: Stephen M. Sorensen, Cincinnati, Ohio

[73] Assignee: Merrell Dow Pharmaceuticals Inc., Cincinnati, Ohio

[21] Appl. No.: 262,168

[22] Filed: Oct. 18, 1988

Related U.S. Application Data

[63] Continuation of Ser. No. 123,755, Nov. 23, 1987, abandoned.

[51] Int. Cl.$^4$ ............................................ A61K 31/445
[52] U.S. Cl. ..................................................... 514/317
[58] Field of Search ........................................ 514/317

[56] References Cited

PUBLICATIONS

Chem. Abst. 106-156281U (1987).
*Fibromyalgia Syndrome An Emerging but Controversial Condition*, JAMA, May 22/29, 1987, vol. 257 No. 20, p. 2782, Don L. Goldenberg, M.D.
*Current Issues Concerning Management of the Fibrositis/-Fibromyalgia Syndrome*, The American Journal of Medicine, vol. 81 (suppl 3A) p. 15, Sep. 29, 1986, Robert Bennett, M.D.
*The Clinical Syndrome of Fibrositis*, The American Journal of Medicine, vol. 81 (suppl 3A) p. 7, Sep. 26, 1986, Frederick Wolfe, M.D.
U.S. Patent Application Ser. No. 71,524 which was filed on Jul. 7, 1987 by A. Carr, et al.

*Primary Examiner*—Stanley J. Friedman
*Attorney, Agent, or Firm*—J. Michael Dixon

[57] ABSTRACT

The present invention relates to a method for relieving or alleviating the symptomatology associated with fibromyalgia comprising administering to a patient a compound as described by Formula I.

8 Claims, No Drawings

TREATMENT OF FIBROMYALGIA

This is a continuation of application Ser. No. 123,755, filed Nov. 23, 1987, now abandoned.

The present invention relates to a method for the treatment of fibromyalgia.

Fibromyalgia is a chronic disease afflicting up to 6 million persons in the United States. Patients suffering from this disease are afflicted with numerous symptoms such as, for example, widespread generalized musculoskeletal pains, aching, fatigue, morning stiffness, and a sleep disturbance which can be characterized as an inadequacy of stage 4 sleep. Often, patients are afflicted with these symptoms for years.

The medical community has not discovered the cause of this disease, nor have they discovered a cure. Clinicians have attempted to treat the symptoms of this disease with nonsteroidal anti-inflammatory agents, corticosteroids, and injections of local anesthetics. Unfortunately, none of these treatments have been successful in relieving or alleviating patients symptoms.

Thus, it would be a valuable contribution to the art to develop a method for alleviating or relieving the symptomatology associated with fibromyalgia.

In accordance with the present invention, it has been discovered that it is possible to treat, that is, relieve or alleviate the symptomatology associated with fibromyalgia in a patient in need thereof, by the administration of a compound of the formula

FORMULA I

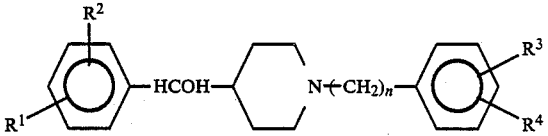

wherein: each of $R^1$, $R^2$, $R^3$, and $R^4$ is independently selected from the group consisting of hydrogen, a $C_{1-6}$ alkyl group, halogen, trifluoromethyl, hydroxy, a $C_{1-6}$ alkoxy group, or an amino group; n is 2, 3, or 4; and the pharmaceutically acceptable acid addition salts thereof.

As used in this application:

(a) The term $C_{1-6}$ alkyl refers to an alkyl group containing up to 6 carbon atoms. Representative examples of suitable alkyl groups include, methyl, ethyl, propyl, isopropyl, n-butyl, t-butyl, pentyl, hexyl, cyclopropyl, and cyclopentyl. Methyl and ethyl are currently preferred.

(b) The term halogen refers to a fluorine, bromine, chlorine or iodine atom. Fluorine and bromine are currently preferred.

(c) The term $C_{1-6}$ alkoxy refers to an alkoxy group containing up to 6 carbon atoms. Representative examples of suitable alkoxy groups include methoxy, ethoxy, propoxy, isopropoxy, butoxy, pentoxy, and hexoxy.

(d) The term hydroxy in this application refers to the following substituent —OH.

(e) The term amino refers to —$NH_2$.

(f) The term "patient" as used herein is taken to mean warm-blooded animals, such as mammals, for example, dogs, rats, mice, cats, guinea pigs, horses, cattle, sheep and primates, including humans.

The expression "pharmaceutically acceptable acid addition salts" is intended to apply to any non-toxic organic or inorganic acid addition salt of the base compounds represented by Formula I. Illustrative inorganic acids which form suitable salts include hydrochloric, hydrobromic, sulfuric and phosphoric acid and acid metal salts such as sodium monohydrogen orthophosphate and potassium hydrogen sulfate. Illustrative organic acids which form suitable salts include the mono-, di- and tri-carboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicyclic, 2-phenoxybenzoic and sulfonic acids such as methane sulfonic acid and 2-hydroxyethane sulfonic acid.

Some of the compounds represented by Formula I exist as optical isomers. Any reference in this application to the compounds of Formula I, is meant to encompass a specific isomer or a mixture of isomers.

In those instances where $R^1$–$R^4$ are other than hydrogen, the substituents may be located at any position of the phenyl ring (i.e., meta, para, or ortho). Para is currently preferred for monosubstituted phenyl moieties. The 2,3-, 2,4- 2,5-, 3,4-, or 3,5-, disubstituted phenyl moieties are also embraced herein.

$R^1$, $R^2$, $R^3$, and $R^4$ can be the same substituents or differing substituents.

It is currently preferred for n to be either 2 or 3, with 2 being most preferred. It is also currently preferred for $R^3$ and $R^4$ to be hydrogen.

Representative examples of preferred compounds include:

(i) alpha-phenyl-1-(2-phenethyl)-4-piperidine methanol;
(ii) alpha-phenyl-1-(3-phenpropyl)-4-piperidine methanol;
(iii) alpha-(4-methylphenyl)-1-(2-phenethyl)-4-piperidine methanol;
(iv) alpha-(4-methoxyphenyl)-1-(2-phenethyl)-4-piperidine methanol;
(v) alpha-(3,5-dimethylphenyl)-1-(2-phenethyl)-4-piperidine methanol;
(vi) alpha-(3-(trifluoromethyl)phenyl)-1-(2-phenethyl)-4-piperidine methanol;
(vii) alpha-(2,3-dimethoxylphenyl)-1-(2-phenethyl)-4-piperidine methanol.

The compounds of Formula I, their methods of preparation and their use as serotonin $5HT_2$ antagonists are known in the art. European Patent Application 0 208 235 discloses these compounds and several methods for preparing these compounds. Any of these methods, or any other method known in the art, are suitable for preparing the compounds to be utilized in the method of the present invention.

The compounds of Formula I will relieve or alleviate the symptoms that patients afflicted with fibromyalgia commonly experience. Thus, patients afflicted with fibromyalgia who are administered, an antifibromyalgia amount of one of the compounds of Formula I will report a significant decrease in the amount of generalized pain they experience, as well as a decrease in morning stiffness and fatigue. Patients will also experience a decreased incidence of sleeping disorders.

The compounds of Formula I can be administered either parenterally or orally.

An effective antifibromyalgia amount of compound required to produce this decrease in symptomatology will vary with the severity of the disease, the patient, the presence of other underlying disease states in the patient, the route of administration, and the particular compound utilized. Generally, a patients symptomatology will respond to a dosage range of from 1-100 mg/kg/day when administered orally and from 0.1-10 mg/kg/day when administered parenterally.

The compounds of Formula I can be compounded into a variety of dosage forms, such as for example, tablets, capsules, solutions, elixirs, sterile solutions for injection and sustained release preparations. Methods for producing these dosage forms are well known in the art and are disclosed in European Patent Application 0208235.

What is claimed is:

1. A method for relieving or alleviating the symptomatology of fibromyalgia in a patient in need thereof comprising administering thereto an antifibromyalgia amount of a compound of the formula:

FORMULA I

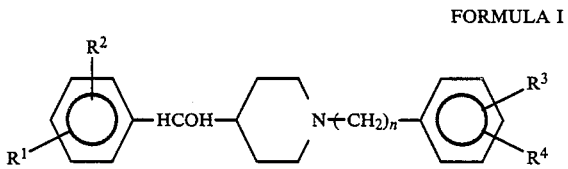

wherein: each of $R^1$, $R^2$, $R^3$, and $R^4$ are independently selected from the group consisting of hydrogen, a $C_{1-6}$ alkyl group, halogen, trifluoromethyl, hydroxy, a $C_{1-6}$ alkoxy group, and an amino group; n is 2, 3, or 4; and the pharmaceutically acceptable acid addition salts thereof.

2. A method according to claim 1, wherein said compound is alpha-phenyl-1-(2-phenethyl)-4-piperidine methanol.

3. A method according to claim 1, wherein said compound is alpha-phenyl-1-(3-phenpropyl)-4-piperidine methanol.

4. A method according to claim 1, wherein said compound is alpha-(4-methylphenyl)-1-(2-phenethyl)-4-piperidine methanol.

5. A method according to claim 1, wherein said compound is alpha-(4-methoxylphenyl)-1-(2-phenethyl)-4-piperidine methanol.

6. A method according to claim 1, wherein said compound is alpha-(3,5-dimethylphenyl)-1-(2-phenethyl)-4-piperidine methanol.

7. A method according to claim 1, wherein said compound is alpha-(3-(trifluoromethyl)phenyl)-1-(2-phenethyl)-4-piperidine methanol.

8. A method according to claim 1, wherein said compound is alpha-(2,3-dimethoxylphenyl)-1-(2-phenethyl)-4-piperidine methanol.

* * * * *